US009781988B2

(12) United States Patent
Washington et al.

(10) Patent No.: US 9,781,988 B2
(45) Date of Patent: *Oct. 10, 2017

(54) APPLIANCE FOR SHAPING FIBROUS MATERIAL

(71) Applicant: The Procter & Gamble Company, Cincinnati, OH (US)

(72) Inventors: Randy Purnell Washington, West Chester, OH (US); Jamie Angel Reed, Maineville, OH (US); Alan David Willey, Cincinnati, OH (US); Stevan A. Samuel, Cincinnati, OH (US); Michael Kloeppel-Riech, Kronberg im Taunus (DE); Sandra Smith, Loveland, OH (US); Frank Beerwerth, Kaltenholzhausen (DE); David Salloum, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/456,632

(22) Filed: Mar. 13, 2017

(65) Prior Publication Data

US 2017/0181516 A1 Jun. 29, 2017

Related U.S. Application Data

(63) Continuation of application No. 14/577,135, filed on Dec. 19, 2014, now Pat. No. 9,713,369.

(Continued)

(51) Int. Cl.
*A45D 2/40* (2006.01)
*A45D 7/06* (2006.01)
(Continued)

(52) U.S. Cl.
CPC ............... *A45D 7/06* (2013.01); *A45D 1/04* (2013.01); *A45D 1/28* (2013.01); *A45D 2/001* (2013.01);
(Continued)

(58) Field of Classification Search
CPC ... A45D 1/04; A45D 1/06; A45D 1/08; A45D 1/14; A45D 1/16; A45D 1/128; A45D 4/12; A45D 4/06; A45D 2/00; A45D 2/001; A45D 2/367; A45D 2/38; A45D 2/40; A45D 6/14; A45D 6/20; A45D 7/00; A45D 7/02; A45D 7/04; A45D 7/06;
(Continued)

(56) References Cited

U.S. PATENT DOCUMENTS 8,035,061 B2 * 10/2011 Jung ................. A45D 1/04
132/223
8,349,780 B2  1/2013 Baker
(Continued)

FOREIGN PATENT DOCUMENTS

CN       201504727 U   6/2010
WO    WO2013142497 A1  9/2013

*Primary Examiner* — Rachel Steitz
(74) *Attorney, Agent, or Firm* — Angela K. Haughey

(57) ABSTRACT

An appliance for shaping fibrous material where when the applicance is in the closed position, the portion of the fibrous material received between the first inner face and the second inner face can receive light energy from the light source and heat energy from the heating element. Also a method, use and kit.

18 Claims, 11 Drawing Sheets

Related U.S. Application Data

(60) Provisional application No. 61/918,159, filed on Dec. 19, 2013.

(51) Int. Cl.
    *A45D 1/04*    (2006.01)
    *A45D 1/28*    (2006.01)
    *A45D 2/00*    (2006.01)
    *A45D 6/20*    (2006.01)
    *A45D 1/00*    (2006.01)

(52) U.S. Cl.
    CPC .......... *A45D 6/20* (2013.01); *A45D 2001/004* (2013.01); *A45D 2001/045* (2013.01)

(58) Field of Classification Search
    CPC .......... A45D 2001/004; A45D 2200/25; A45D 2200/205; A61Q 5/04; A61Q 5/06; A61N 5/0616; A61N 5/0617
    See application file for complete search history.

(56) References Cited

U.S. PATENT DOCUMENTS

| | | |
|---|---|---|
| 8,883,710 B2 | 11/2014 | Willey |
| 2004/0000319 A1 | 1/2004 | Carballada |
| 2004/0206368 A1 | 10/2004 | Warner |
| 2006/0196523 A1* | 9/2006 | Choi .................. A45D 1/04 132/224 |
| 2009/0145452 A1 | 6/2009 | Anderson |
| 2009/0285768 A1 | 11/2009 | Baker |
| 2010/0101598 A1 | 4/2010 | Ng |
| 2010/0132733 A1 | 6/2010 | Kyu |
| 2010/0269848 A1 | 10/2010 | Morgandi |
| 2011/0120491 A1 | 5/2011 | You |
| 2012/0291797 A1* | 11/2012 | deGrood ................ A45D 1/28 132/211 |
| 2013/0192625 A1 | 8/2013 | Migliori |
| 2015/0096584 A1 | 4/2015 | Washington |
| 2015/0173478 A1 | 6/2015 | Adams |
| 2015/0173479 A1 | 6/2015 | Adams |
| 2015/0174023 A1 | 6/2015 | Washington |
| 2015/0174027 A1 | 6/2015 | Washington |
| 2015/0174028 A1 | 6/2015 | Washington |
| 2015/0174029 A1 | 6/2015 | Washington |
| 2015/0174030 A1 | 6/2015 | Washington |
| 2015/0174031 A1 | 6/2015 | Washington |
| 2015/0174032 A1 | 6/2015 | Washington |
| 2015/0174035 A1 | 6/2015 | Reed |
| 2015/0174036 A1 | 6/2015 | Washington |
| 2015/0174037 A1 | 6/2015 | Washington |
| 2015/0174432 A1 | 6/2015 | Adams |
| 2015/0174793 A1 | 6/2015 | Adams |

* cited by examiner

A-A

B-B

C-C

APPLIANCE FOR SHAPING FIBROUS MATERIAL

FIELD OF THE INVENTION

An appliance for shaping fibrous material wherein when the applicance is in the closed position, the portion of the fibrous material received between the first inner face and the second inner face can receive light energy from the light source and heat energy from the heating element.

BACKGROUND OF THE INVENTION

Appliances for shaping fibrous material include for example fabric irons, hair curling tongs, hair straightening irons. Modem appliances typically have temperature controls so the user can select an appropriate heat setting for their needs and thus avoid unnecessarily high temperatures that may damage the fibrous material. The temperature may be indicated with a dial or via LED indicator lights on the handle. Heat protection sprays may also be recommended for pre-treatment of the fibrous material to be treated. Where the appliance is passed over the fibrous material, a special coating may be used on the appliance area that directly contacts the fibrous material to reduce friction damage.

CN201504727U discloses a infrared pull-free hair straightening clamp characterized by no pull force, small electricity consumption and reduced hair damage in perming, comprising an upper clamp body, a lower clamp body, a perming plate, a heater and a temperature control device, wherein the upper clamp body and the lower clamp body are hinged to form a pincer-shaped fixture; the perming plate is installed on the inner side surface of the lower clamp body; the heater is a PTC heater installed in a heat-conductive, high temperature-resistant cylinder; and there is a groove on the upper clamp body rightly opposite the perming plate; the heat-conductive, high temperature-resistant cylinder is movably installed on the supports at both ends of the groove, the surface of the heat-conductive, high temperature-resistant cylinder being higher than the inner side surface of the upper clamp body; there are also grooves on the edges of both sides of the supper clamp body, and a plurality of infrared LED lights are installed in the grooves. US20040206368A1 mentions a device used for straightening hair. US20040206368A1 states that the "device includes a handle 40 and a flat transparent plate 42 . . . [and the] plate can be passive and merely transmit light of the proper radiation generated by a UV lamp or other light source, or active and generate and emit light 41 from inside the plate 42 as described . . . for the light-emitting hair curler".

There is a constant need for improved appliances for shaping fibrous material. More specifically there is a need for appliances enabling reduced heat damage of the fibrous material.

SUMMARY OF THE INVENTION

A first aspect of the invention relates to an appliance 1 for shaping fibrous material 4 comprising:
- a first arm 2 pivotable with respect to a second arm 3, the first arm 2 and the second arm 3 thereby configured to form a clamp for receiving fibrous material 4 positioned between the first and second arms 2, 3 when the appliance is in a closed position;
- wherein the first arm 2 comprises a first inner face 5 which faces the second arm 3;
- and wherein the second arm 3 comprises a second inner face 6 which faces the first inner face 5 on the first arm 2;
- and wherein a first plate 7 extends upon a portion of the first inner face 5;
- and wherein a second plate 7 extends upon a portion of the second inner face 6;
- wherein both the first plate 7 and the second plate 7 are substantially flat;
- wherein a heating element 9 is provided in at least one of the first arm 2 and/or the second arm 3;
- wherein at least one light source 10 is provided in at least one of the first arm 2 and/or the second arm 3;
- and wherein the first inner face 5 and/or the second inner face 6 respectively comprise a heat-transmitting area 11 and/or a light-transmitting area 12;
- and wherein the heating element 9 is located proximal to the heat-transmitting area 11 and wherein the light source 10 is located proximal to the light-transmitting area 12;

and wherein when the appliance 1 is in the closed position, the portion of the fibrous material 4 received between the first inner face 5 and the second inner face 6 can receive light energy from the light source 10 and heat energy from the heating element 9.

A second aspect of the invention relates to a method for shaping fibrous material 4 comprising:
- applying to fibrous material 4 a crosslinking composition comprising a photocatalyst and an active agent capable of crosslinking fibrous material 4; and then
- shaping the fibrous material with the appliance 1 according to the first aspect.

A third aspect of the invention relates to the use of the appliance 1, according to the first aspect, for shaping fibrous material 4, preferably straightening hair.

A fourth aspect of the invention relates to a kit comprising:
- the appliance 1 according to the first aspect;
- a crosslinking composition comprising a photocatalyst and an active agent capable of crosslinking fibrous material 4.

DETAILED DESCRIPTION OF THE INVENTION

Definitions and General

Figure 1:
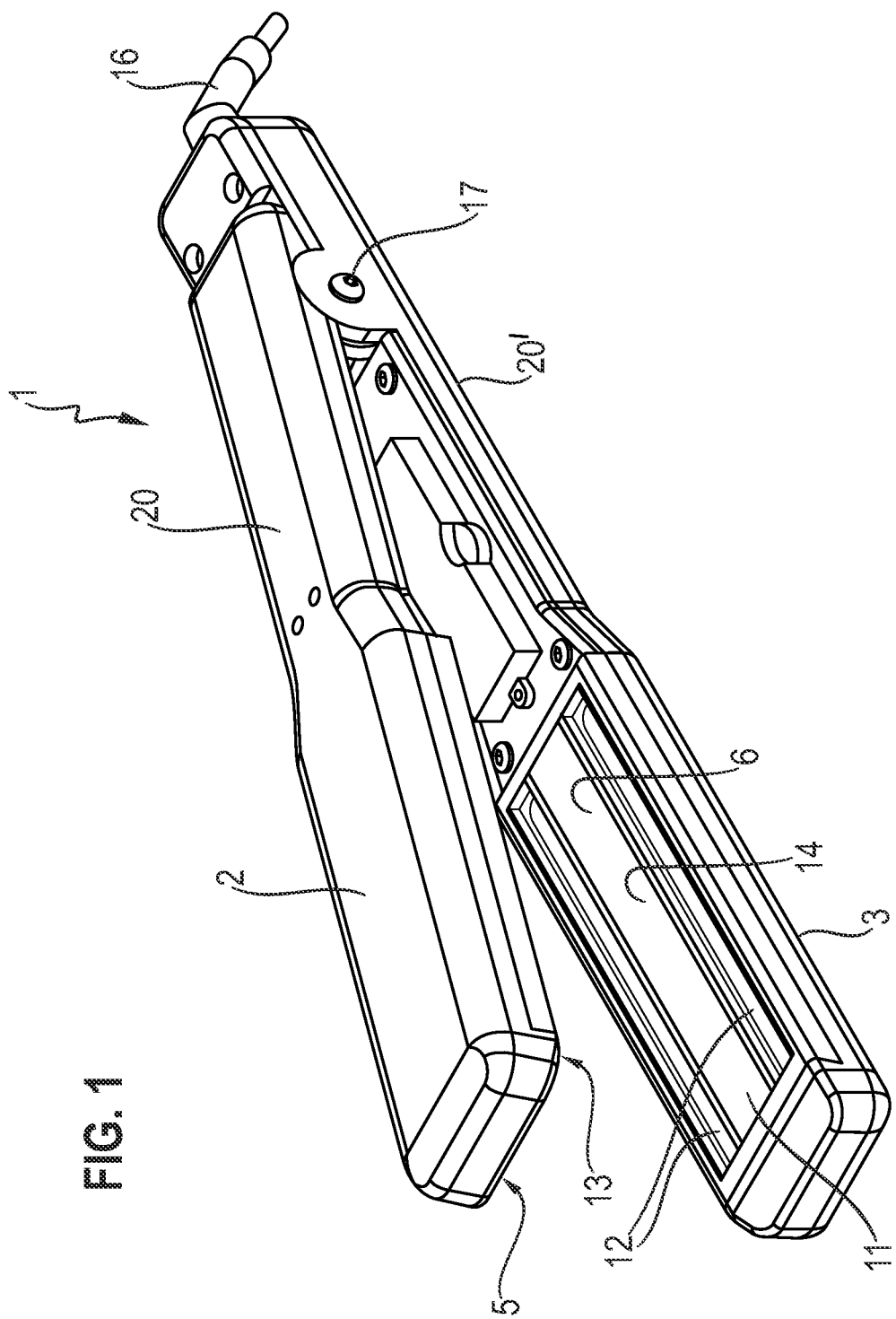
FIG. 1: Shows a perspective view of an appliance according to the present invention.
Figure 2:
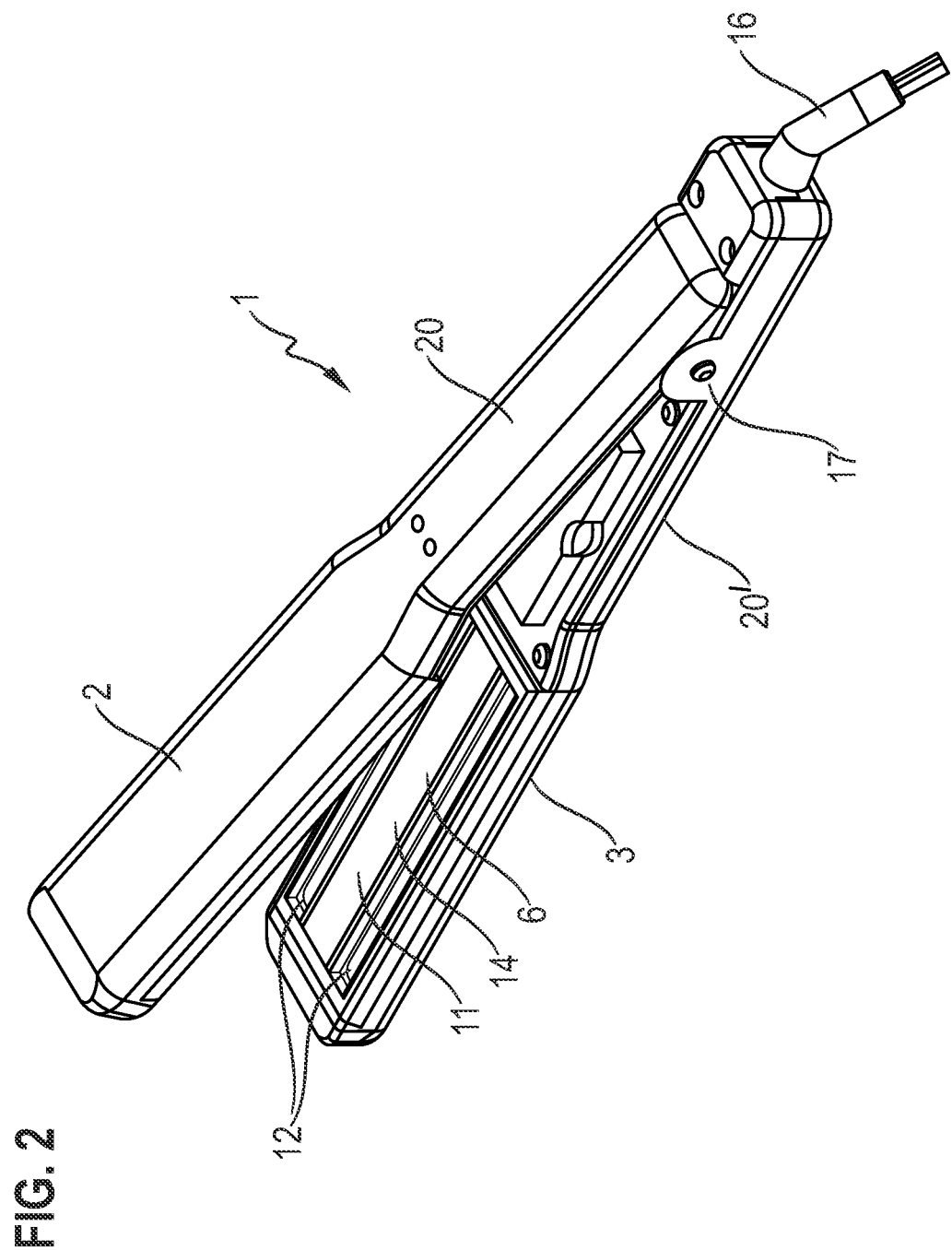
FIG. 2: Shows a perspective view of an appliance according to the present invention.
Figure 3:
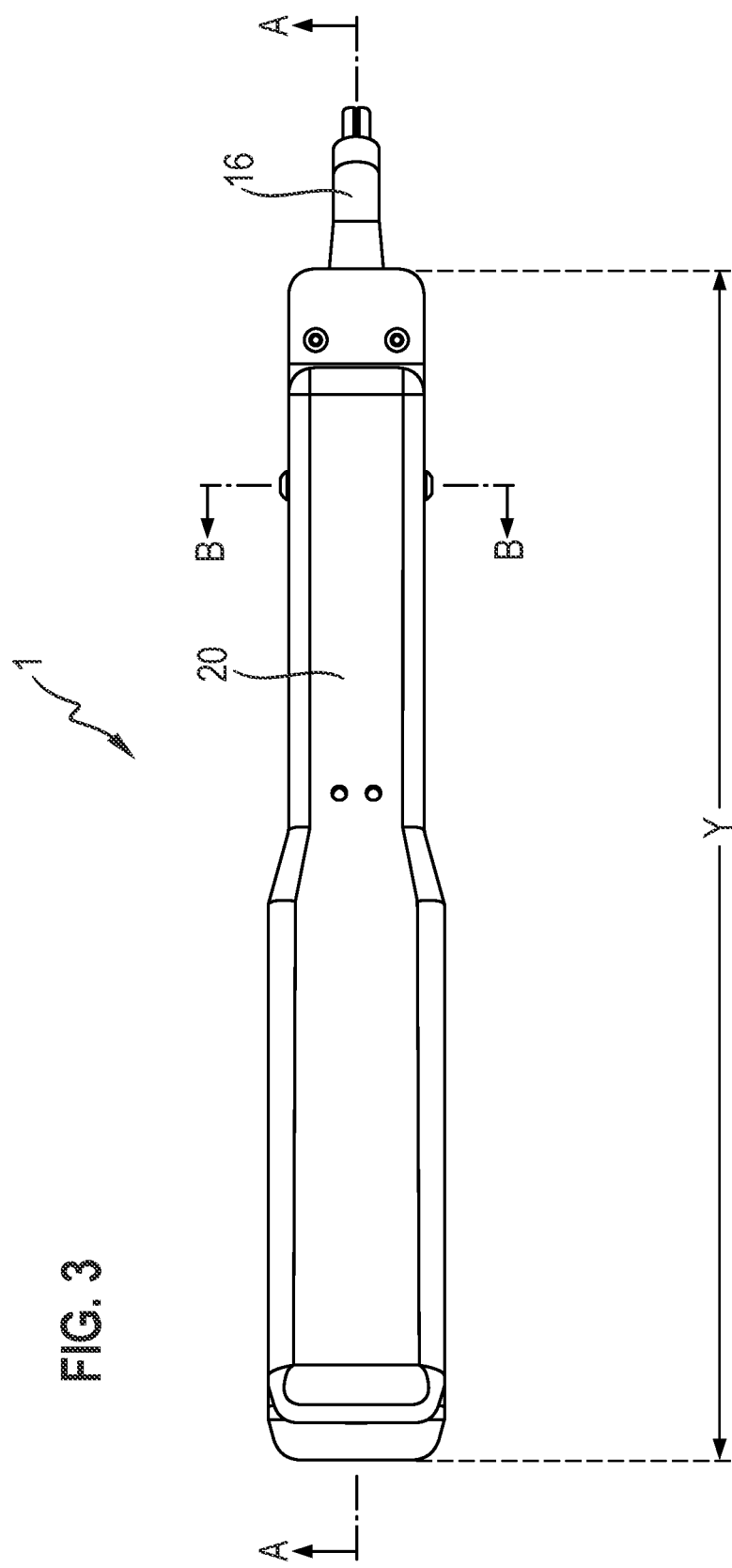
FIG. 3: Shows a perspective view from above of an appliance according to the present invention.
Figure 4:
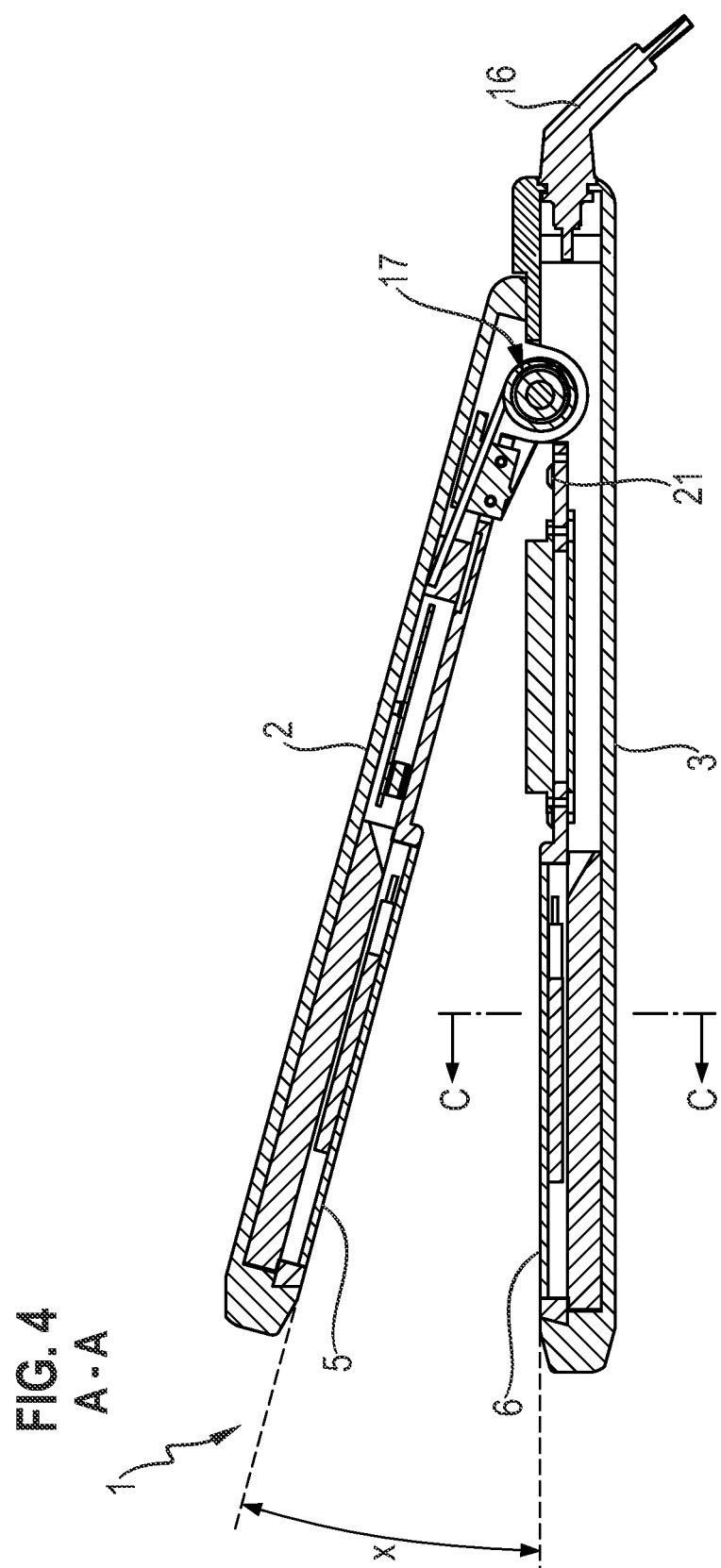
FIG. 4: Shows a sectional view across section A-A of an appliance according to the present invention. Section A-A is depicted in FIG. 3.
Figure 5:
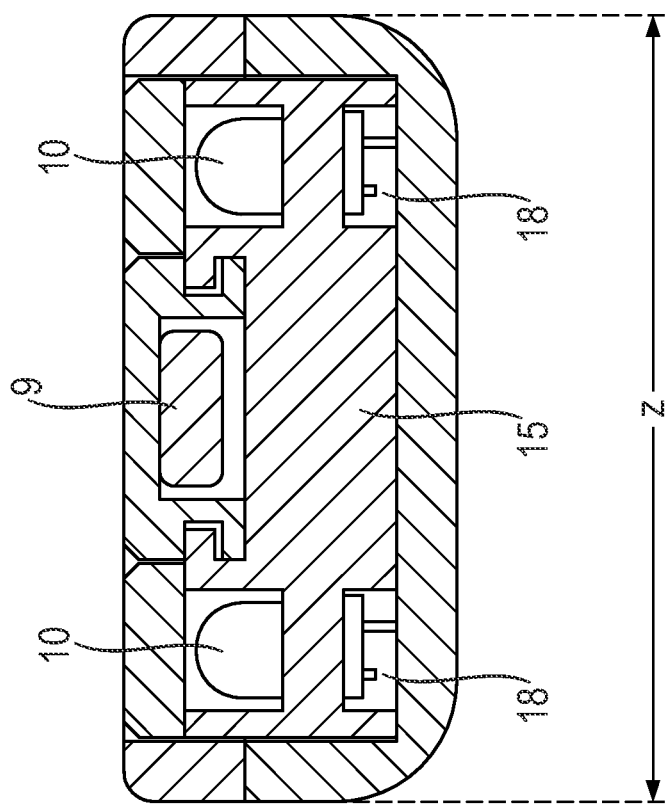
FIG. 5: Shows a sectional view across section C-C of an appliance according to the present invention. Section C-C is depicted in FIG. 4.
Figure 6:
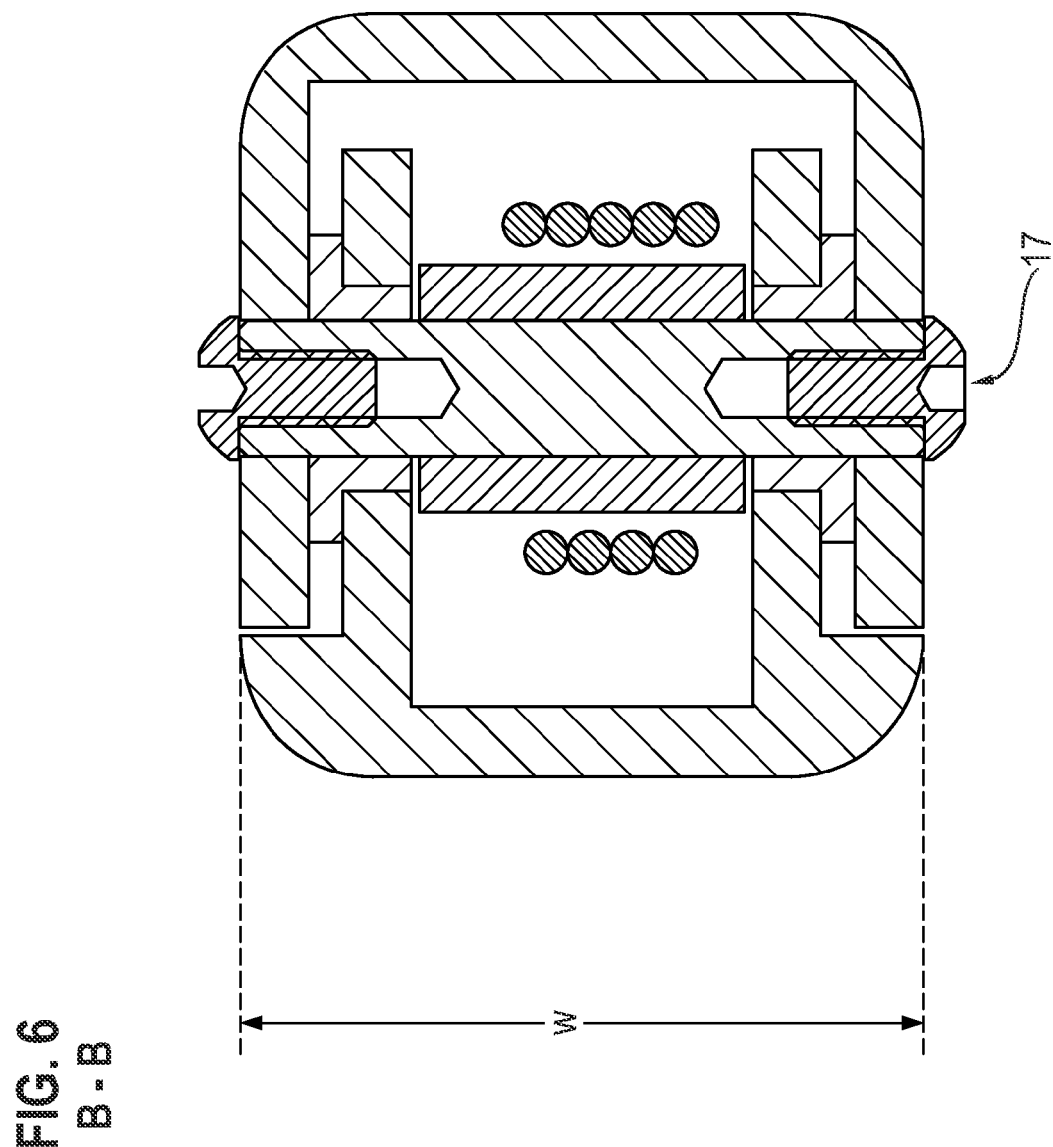
FIG. 6: Shows a sectional view across section A-A of an appliance according to the present invention. Section B-B is depicted in FIG. 3.

In this document, including in all embodiments of all aspects of the present invention, the following definitions apply unless specifically stated otherwise. All percentages are by weight of the total composition. All ratios are weight ratios. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 23° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein "min" means "minute" or "minutes". Herein "mol" means mole. Herein "g" following a number means "gram" or "grams". All weights as they pertain to listed ingredients are based on the active level and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, where the composition comprises from about 1% to about 5% fatty alcohol, then a composition comprising 2% stearyl alcohol and 1% cetyl alcohol, would fall within the scope.

"Molecular weight" or "M·Wt." or "MW" and grammatical equivalents mean the number average molecular weight.

"Viscosity" is measured at 25° C. using a HAAKE Rotation Viscometer VT 550 with cooling/heating vessel and sensor systems according to DIN 53019 at a shear rate of 12.9 s$^{-1}$.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Dry" or "substantially dry" means comprising less than 5%, less than 3% or, less than 2%, less than 1%, or about 0% of any compound or composition being in liquid form when measured at 25° C. at ambient conditions. Such compounds or compositions being in liquid form include water, oils, organic solvents and other wetting agents. "Anhydrous" means that the composition comprises less than 5%, less than 3% or, less than 2%, less than 1%, or about 0% water by total weight of the composition.

"Substantially free from" or "substantially free of" means less than about 1%, or less than 0.8%, or less than 0.5%, or less than 0.3%, or about 0%, by total weight of the composition or formulation.

"Hair" means mammalian keratin fibres including scalp hair, facial hair and body hair. It includes such hair still being attached to a living subject and also hair that has been removed therefrom such as hair swatches and hair on a doll/mannequin. In at least one embodiment, "hair" means human hair. "Hair shaft" or "hair fibre" means an individual hair strand and may be used interchangeably with the term "hair."

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. In at least one embodiment, "derivatives thereof" means the amide, ether, ester, amino, carboxyl, acetyl, acid, salt and alcohol derivatives.

"Kit" means a package comprising a plurality of components. "Kit" may be referred to as "kit-of-parts". An example of a kit is, for example, a first composition and a separately packaged second composition and optionally application instructions.

Explanation of the Invention

The inventors have surprisingly found that an appliance for shaping fibrous material can be provided that enables low heat shaping of fibrous material and thus enables reduced damage to the fibrous material. The lower heat is enabled by using light-initiated chemistry on the fibrous material. The light-initiated chemistry uses a photocatalyst and an active agent capable of crosslinking fibrous material. A photocatalyst is an acid or base (or conjugate thereof) having a pKa (or pKb) value that decreases (or increases) upon exposure to electromagnetic radiation, particularly light. Photoacids are a type of photocatalyst and are described in: Domcke and Sobolewski (2003), Unraveling the Molecular Mechanisms of Photoacidity, 302, p. 1693 and in Kowalewska (2005), *Photoacid catalyzed sol-gel process*, J. Mater. Chem. 15, p. 4997, which are both incorporated herein by reference. When the applicance 1 of the present invention is in the closed position, the portion of the fibrous material 4 received between the first inner face 5 and the second inner face 6 can receive light energy from the light source 10 and heat energy from the heating element 9. This appliance design means that the light-initiated chemistry can be applied to the fibrous material and then the appliance used such that good shaping efficacy and shaping durability is resultant using a lower heat setting than with conventional appliances. Previous devices have not offered the combination of light and possibility for low heat; and in combination with a light-initiated chemistry, the device allows for efficacious styling, while reducing the amount of heat damage to the fibrous material, which is often characterised by reduced protein loss as a result of less heat damage.

The first aspect relates to an appliance 1 for shaping fibrous material 4. This aspect and other aspects of the present invention are described in more detailed hereinafter.

Appliance

The appliance 1 is for shaping fibrous material 4. In at least one embodiment, the appliance 1 is for shaping keratin fibres. In at least one embodiment, the keratin fibres are selected from the group consisting of: human scalp hair, human facial hair, and human eyelashes. In at least one embodiment, the shaping is straightening or curling.

In at least one embodiment, the appliance 1 comprises an electrical cable 16. In at least one embodiment, the appliance 1 is cable-free. In the cable-free embodiment, the appliance comprises a rechargeable battery. A cabled appliance is useful because of the lack of need for a battery, which may be heavy for the consumer and also due to the lack of battery-life limitation during use.

In at least one embodiment, the appliance 1 has a length Y. The length Y excludes any electrical cable 16. In at least one embodiment, the length Y is from about 5 cm to about 25 cm, or from about 7 cm to about 20 cm, or from about 10 cm to about 15 cm.

In at least one embodiment, the appliance 1 has a width Z. The width Z is not in the handle portions 20, 20' of the appliance 1. In at least one embodiment, the width Z is from about 0.5 cm to about 10 cm, or from about 1 cm to about 5 cm, or from about 1 cm to about 2 cm. In at least one embodiment, the appliance 1 has a width W. The width W is at the handle portions 20, 20' of the appliance 1. In at least one embodiment, the width W is from about 0.5 cm to about 10 cm, or from about 1 cm to about 5 cm, or from about 1 cm to about 2 cm.

The appliance 1 comprises a first arm 2 pivotable with respect to a second arm 3, the first arm 2 and the second arm 3 thereby configured to form a clamp for receiving fibrous material 4 positioned between the first and second arms 2, 3 when the appliance is in a closed position. In at least one embodiment, the the first arm 2 and the second arm 3 each comprise a handle portion 20, 20' being distal from the heat-transmitting area 11. In at least one embodiment, the first arm 2 and the second arm 3 are connected by a hinge 17, and wherein a handle portion of each arm 20, 20' is proximal to the hinge 17. In at least one embodiment, the hinge 17 is spring-loaded.

In at least one embodiment, the appliance 1 in an open position has an angle X. The open position is characterised in that the first plate 7 and the second plate 7 are not juxtaposed. In at least one embodiment, the angle X is from about 5° to about 70°, or from about 8° to about 30°, or from about 10° to about 20°.

In at least one embodiment, the appliance 1 comprises a housing material. The housing material may be an insulator. In at least one embodiment, the housing material is composed of plastics.

Plates

A first plate 7 extends upon a portion of the first inner face 5 and a second plate 7 extends upon a portion of the second inner face 6. Both the first plate 7 and the second plate 7 are substantially flat. In at least one embodiment, the first plate 7 and the second plate 7 are flat. In at least one embodiment, the first plate 7 and the second plate 7 are planar.

The first inner face 5 and/or the second inner face 6 respectively comprise a heat-transmitting area 11 and/or a light-transmitting area 12. In at least one embodiment, the first inner face 5 comprises a heat-transmitting area 11 and a light-transmitting area 12. In at least one embodiment, the second inner face 6 comprises a heat-transmitting area 11 and a light-transmitting area 12. In at least one embodiment, the first inner face 5 comprises a heat-transmitting area 11 and a light-transmitting area 12, and wherein the second inner face 6 comprises a heat-transmitting area 11 and a light-transmitting area 12. In at least one embodiment, the first inner face 5 comprises a heat-transmitting area 11 and the second inner face 6 comprises a light-transmitting area 12. For the insulation of the light-source 10 from the heating element 9, it is useful to have the light-transmitting area 12 on one arm of the appliance and the heat-transmitting area 11 on the other arm of the appliance.

In at least one embodiment, the first plate 7 and/or the second plate 7 are composed of metal. In at least one embodiment, the first plate 7 and/or the second plate 7 are composed of ceramic. Ceramic has the advantage that it is a very smooth and flat surface and is resistant to chemical damage. In at least one embodiment, the ceramic is transparent to infra-red radiation. With the same principles as a ceramic hob for a cooker, the first plate 7 and/or the second plate 7 are composed of ceramic enables the use of a heating element 9 being an infra-red heater such that the heating element 9 shines infra-red radiation through the ceramic in order to heat up the fibrous material 4. In at least one embodiment, the first plate 7 and/or the second plate 7 are composed of aluminium or aluminium alloy. Aluminium has the benefit of being relatively light in weight.

Figure 7:
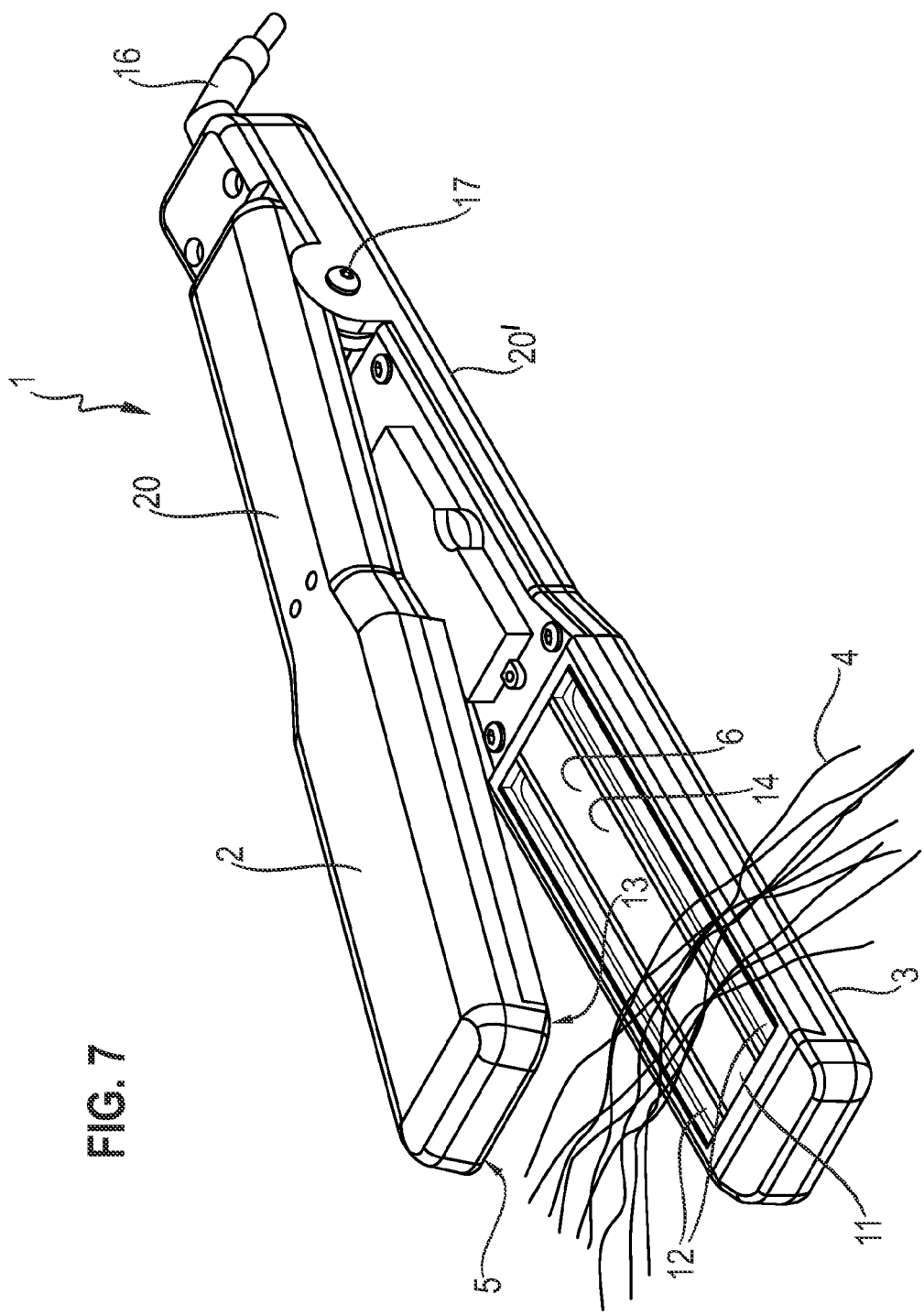
FIG. 7: Shows a perspective view of an appliance according to the present invention.
Figure 8:
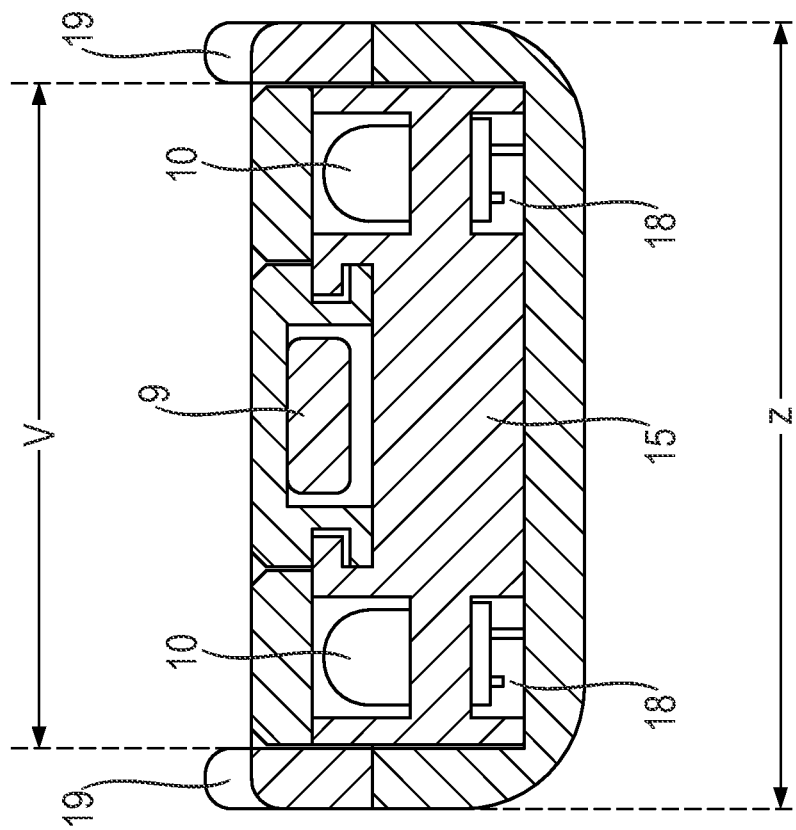
FIG. 8: Shows a sectional view across section C-C of an alternative appliance according to the present invention. Section C-C is depicted in FIG. 4.
Figure 9:
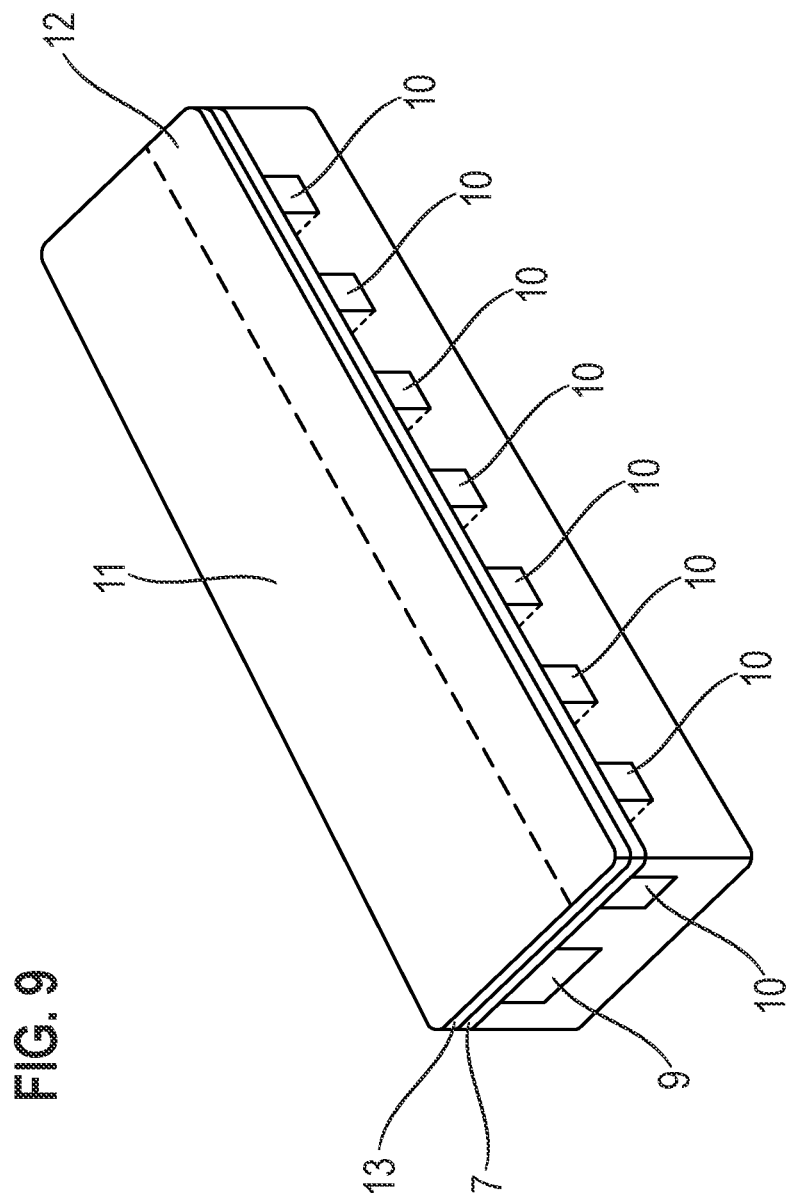
FIG. 9: Shows a portion of an appliance according to the present invention.
Figure 10:
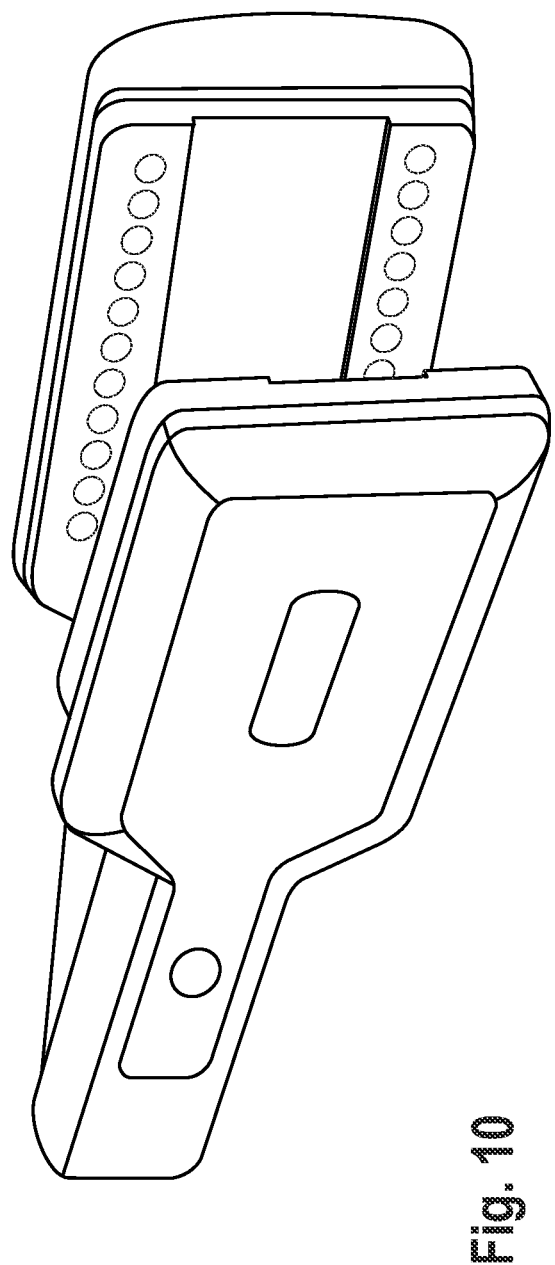
FIG. 10: Shows a perspective view of an appliance according to the present invention.

In at least one embodiment, the first plate 7 has a first top surface 13. In at least one embodiment, the second plate 7 has a second top surface 13. The first and second top surfaces 13 are in direct contact with the fibrous material 4, for example keratin fibres, when the appliance has received the fibrous material 4, for example keratin fibres, positioned between the first and second arms 2, 3. See for example, FIG. 7.

In at least one embodiment, the first and second top surfaces 13 are composed of enamel. In at least one embodiment, the first and second top surfaces 13 are composed of ceramic. In at least one embodiment, the first and second top surfaces 13 are composed of anodised aluminium. In at least one embodiment, the first and second top surfaces 13 are composed of a silicon-based lacquer, or a silicone-based lacquer. In at least one embodiment, the first and second top surfaces 13 in the light-transmitting area 12 are translucent and/or transparent.

In at least one embodiment, the first and second top surfaces 13 are a symmetrical pair in appearance.

In at least one embodiment, the first and second top surfaces 13 have an average roughness value Ra, measured over a reference length of 1.25 mm, being from about 0.1 μm to about 1 μm, or from about 0.1 μm to 0.3 μm, or from about 0.2 μm to about 0.3 μm. Roughness is quantified by the vertical deviations of a surface from its ideal (smooth) form. Roughness value Ra is calculated by the formula:

$$R_a = \frac{1}{n}\sum_{i=1}^{n}|y_i|$$

Said calculation is described in DeGarmo, E. Paul, Black, J. T., Kohser, Ronald A. (2003), *Materials and Processes in Manufacturing* (9th ed.), Wiley, p. 223, ISBN 0-471-65653-4. In at least one embodiment, the heat-transmitting area 11 and a light-transmitting area 12 have a roughness value Ra, measured over a reference length of 1.25 mm, being from about 0.1 μm to about 1 μm, or from about 0.1 μm to 0.3 μm, or from about 0.2 μm to about 0.3 μm.

In at least one embodiment, the first and second plates 7 have a width of from about 1 cm to about 5 cm, or from about 1.5 cm to about 4.5 cm, or from about 2 cm to about 4 cm, or from about 2.5 cm to about 3.5 cm. The width of the plate is measured perpendicular to the length of the arm. In at least one embodiment, at least the first plate 7 and/or second plate 7 has/have a width V. In at least one embodiment, the width V is from about 0.5 cm to about 10 cm, or from about 1 cm to about 5 cm, or from about 1 cm to about 2 cm. Wider plates are generally preferred by consumers in view of generally requiring less passes to straighten the hair. This is especially the case where consumers have longer hair than average.

In at least one embodiment, the heat-transmitting area 11 or the fibrous material 4 can be heated to a temperature of from about 50° C. to about 180° C. In at least one embodiment, the heat-transmitting area 11 or the fibrous material 4 can be heated to a temperature of from about 100° C. to about 150° C.

Light Source

In at least one embodiment, the light source 10 is at least one light-emitting diode (LED) or at least one arc light. LEDs are useful because they operate on low amounts of power. In at least one embodiment, the LED has an electrical connection for the LED 18. The LED may be 3 mm T–1 or 5 mm T–1¾.

In at least one embodiment, the light source 10 is capable of emitting radiation with a wavelength from about 300 nm to about 800 nm. In at least one embodiment, the light source 10 is capable of emitting light having a wavelength of from about 315 nm to about 450 nm, or from about 350 nm to about 440 nm.

In at least one embodiment, the light source 10 is at least one light-emitting diode, or a plurality of light-emitting diodes disposed along at least a portion of the length of the first and/or second arm 2, 3. In at least one embodiment, the light source 10 comprises at least two arrays of light-emitting diodes, wherein each array is a plurality of light-emitting diodes disposed along at least a portion of the length of the first and/or second arm 2, 3. In at least one embodiment, each array comprises at least 3, or at least about 4, or at least about 5, or at least about 6, or at least about 7, or at least about 8, or at least about 9, or at least about 10, or at least about 11 light-emitting diodes. In at least one embodiment, each array comprises less than 20, or less than 15 light-emitting diodes. In at least one embodiment, the appliance comprises from about 2 to about 6 arrays of light-emitting diodes.

Irradiance, that is the power of electromagnetic radiation in Watts per unit area, has the unit Watts per $m^2$ or $W/m^2$. Irradiance is thus a measurement of the intensity of electromagnetic radiation. Light intensity can also be measured in lux (lx), which is the unit of illuminance. 1 lx=about $1.5 \times 10^{-7}$ $W/cm^2$ (at 555 nm). An average laboratory or office space would have a light intensity of about 200 lx to about 1000 lx i.e. an irradiance of about $2.9 \times 10^{-5}$ $W/cm^2$ to about $1.4 \times 10^{-4}$ $W/cm^2$ (at 555 nm). In at least one embodiment, the light source 10 has an irradiance of at least about $1 \times 10^{-3}$ $W/cm^2$, or at least about $5 \times 10^{-3}$ $W/cm^2$, or at least about $1 \times 10^{-2}$ $W/cm^2$, or at least about $5 \times 10^{-2}$ $W/cm^2$, or at least about $1 \times 10^{-1}$ $W/cm^2$, or at least about $5 \times 10^{-1}$ $W/cm^2$. In at least one embodiment, the light source 10 has an illuminance of at least about 1000 lx, or at least about 2000 lx, or at least about 3000 lx, or at least about 4000 lx, or at least about 5000 lx, or at least about 6000 lx, or at least about 7000 lx, or at least about 8000 lx, or at least about 9000 lx, or at least about 10000 lx, or at least about 20000 lx, or at least about 30000 lx, or at least about 40000 lx, or at least about 50000 lx, or at least about 60000 lx, or at least about 70000 lx, or at least about 80000 lx.

Radiant power is the measure of the total power of electromagnetic radiation (including infrared, ultraviolet, and visible light) and is a measure of the radiant energy per unit time. Radiant power is measured in Watts, W. In at least one embodiment, the light source 10 has a radiant power of at least about 20 mW, or at least about 30 mW, or at least about about 40 mW, or at least about 50 mW.

In at least one embodiment, the appliance comprises a light protection means 19. A light protection means 19 is useful to protect user from light emitted by the light source 10, e.g. from UV light. In other words, such that all light emitted by the light source 10 is received by the fibrous material 4 e.g. keratin fibres. In at least one embodiment, the light protection means 19 surrounds the light source 9 such that substantially all light is received by the light transmitting area 12. In at least one embodiment, the light protection means 19 comprises three elements (a) a limited source angle for light emitted from the light source (b) a light-absorbing element to hinder the passage of light laterally and downwards and (c) an opposing light-absorbing element to hinder the passage of light laterally and upwards.

Switch

In at least one embodiment, the appliance 1 comprises a switch 21 for the light source. In at least one embodiment, the switch 21 for the light source comprises a magnet. In at least one embodiment, the magnet is diposed on one arm and is complementary to a magnetic element on the other arm such that when the appliance is in a closed position, the magnet and the magnetic element are in contact such that an electrical connection is made providing power to the light source 10. In at least one embodiment, the switch for the light source 21 is a reed switch.

In at least one embodiment, when the appliance 1 is in the closed position, the portion of the fibrous material 4 received between the first inner face 5 and the second inner face 6 can simultaneously receive light energy from the light source 10 and heat energy from the heating element 9.

Heating Element

In at least one embodiment, the heating element 9 is a resistive heating element. In at least one embodiment, the heating element 9 is a ceramic heating element. In at least one embodiment, the heating element 9 is an infrared heating element. The infrared heating element has the advantage that it is easier to to control the temperature of the fibrous material received between the first and second arms and the fibrous material heats up more quickly. Moreover, a infrared heating element has the advantage that the infrared heats the fibrous material directly, which means that the heating is less dependent on the speed at which the fibrous material is passed between the first and second arms 2, 3. Furthermore, a infrared heating element has the advantage that less over-heating of the fibrous material is likely. In at least one embodiment, the heating element 9 is provided as a component of a heater assembly. In at least one embodiment, the heater assembly comprises a resistive wire coiled around a mica sheet, which is sandwiched between two further mica sheets. The mica sheet sandwich may be wrapped in an insulating means such as insulating tape and further enclosed in aluminium or aluminium alloy. The heater assembly may be affixed to the first plate 7 and/or second plate 7 and made flat by squashing flat against the first plate 7 and/or second plate 7. In at least one embodiment, the heating element 9 is enclosed in aluminium or aluminium alloy.

In at least one embodiment, the heating element 9 comprises a heating unit, a heat transfer unit and a temperature sensor unit, wherein the heating unit comprises a first composition, the first composition comprising an epoxy-based or glass-based composition or a composition comprising a sol-gel solution in which up to about 90% of said solution is a conductive powder in a uniform stable dispersion and said solution conductive powder is a member selected from the group consisting of metals, ceramics, interceramics and semi-conductors and the temperature sensor comprising a second composition, the second composition comprising an epoxy-based or glass-based composition or a composition comprising a composition comprising a sol-gel solution in which up to about 90% of said solution is a conductive powder in a uniform stable dispersion and said solution conductive powder is a member selected from the group consisting of metals, ceramics, interceramics and semi-conductors, the heating unit and the temperature sensor unit being provided as two units, which are electrically insulated from each other and which are mechanically supported by the heat transfer unit. An example of such a heating element 9 is described in EP2106195B1, which is incorporated herein by reference.

In at least one embodiment, the heating element 9 is heated to a starting temperature and whose temperature is regulated by a temperature control, wherein the appliance 1 has a sensor that measures data from which a parameter based on the condition of the fibrous material 4 can be generated, and wherein the parameter influences the temperature of the heating element 9. Such embodiment, is described in US2012/0055501A1, which is incorporated herein by reference.

Insulating Means

In at least one embodiment, light source 10 is isolated from the heating element 9, or wherein the light source 10 is cooled. In at least one embodiment, the light source 10 is insulated from the heating element 9 and heat-transmitting area 11 or the light source 10 is cooled. In at least one embodiment, the light source 10 is isolated from the heating element 9 and heat-transmitting area 11 via an insulating means 15. In at least one embodiment, the insulating means 15 is an area of air and/or insulating material. In at least one embodiment, the insulating material comprises at least 75% plastics.

In at least one embodiment, the light-transmitting area 12 is not in a plane with the heat-transmitting area 11. In at least one embodiment, the light-transmitting area 12 is not on the same plane as the heat-transmitting area 11.

In at least one embodiment, the first inner face 5 comprises a heat-transmitting area 11 and the second inner face 6 comprises a light-transmitting area 12, and wherein the insultating means 15 is via the heat-transmitting area 11 and light-transmitting area 12 being on separate faces 5, 6.

Where the first and/or second plate 7 are composed of ceramic and the ceramic is transparent to infrared light and wherein the heating element 9 is an infrared heater, then a insulating means 15 is not required.

Operation Modes

In at least one embodiment, the appliance 1 is able to operate in at least a first mode or in a second mode, wherein the second mode is different from the first mode. In at least one embodiment, the appliance 1 comprises at least a first and a second sensor for measuring data, a user interface enabling the user to enter further data and a data processing unit. In at least one embodiment, the data processing unit generates a selection signal for selecting at least either the first or the second mode depending on the data measured by the at least first and second sensors and depending on the user data entered and wherein the first and second sensors are provided to measure temperature and/or hair wetness. In at least one embodiment, the appliance 1 comprises heating or cooling device for use at a given temperature level and wherein the modes are temperature levels. In at least one embodiment, wherein the data entered by the user relates to at least one of hair length, hair density and/or hair color and the sensors being provided to measure a different physical property than that of the data entered via the user interface.

Particular Embodiments

In at least one embodiment, the first aspect relates to an appliance 1 comprising: a first arm 2 pivotable with respect to a second arm 3, the first arm 2 and the second arm 3 thereby configured to form a clamp for receiving fibrous material 4 positioned between the first and second arms 2, 3 when the appliance is in a closed position; wherein the first arm 2 comprises a first inner face 5 which faces the second arm 3; and wherein the second arm 3 comprises a second inner face 6 which faces the first inner face 5 on the first arm 2; and wherein a first plate 7 extends upon a portion of the first inner face 5; and wherein a second plate 7 extends upon a portion of the second inner face 6; wherein both the first plate 7 and the second plate 7 are substantially flat; wherein a heating element 9 is provided in the second arm 3; and wherein the second inner face 6 comprises a heat-transmitting area 11; and wherein at least one light source 10 is provided in the first arm 2; and wherein the first inner face 5 comprises a light-transmitting area 12; and wherein the heating element 9 is located proximal to the heat-transmitting area 11 and wherein the light source 10 is located proximal to the light-transmitting area 12; and wherein when the applicance 1 is in the closed position, the portion of the fibrous material 4 received between the first inner face 5 and the second inner face 6 can receive light energy from the light source 10 and heat energy from the heating element 9.

In at least one embodiment, the first aspect relates to an appliance 1 comprising: a first arm 2 pivotable with respect to a second arm 3, the first arm 2 and the second arm 3 thereby configured to form a clamp for receiving fibrous material 4 positioned between the first and second arms 2, 3 when the appliance is in a closed position; wherein the first arm 2 comprises a first inner face 5 which faces the second arm 3; and wherein the second arm 3 comprises a second inner face 6 which faces the first inner face 5 on the first arm 2; and wherein a first plate 7 extends upon a portion of the first inner face 5; and wherein a second plate 7 extends upon a portion of the second inner face 6; wherein both the first plate 7 and the second plate 7 are substantially flat; wherein a heating element 9 is provided independently in both the first arm 2 and the second arm 3; and wherein both the first inner face 5 and the second inner face 6 independently comprise a heat-transmitting area 11; and wherein at least one light source 10 is provided independently in both the first arm 2 and the second arm 3; and wherein the first inner face 5 and the second inner face 6 independently comprise a light-transmitting area 12; and wherein the respective heating elements 9 are located proximal to the respective heat-transmitting areas 11 and wherein the respective light sources 10 are located proximal to the respective light-transmitting areas 12; and wherein when the appliance 1 is in the closed position, the portion of the fibrous material 4 received between the first inner face 5 and the second inner face 6 can receive light energy from the light source 10 and heat energy from the heating element 9.

$2^{nd}$ Aspect—Method

The second aspect relates to a method for shaping fibrous material 4 comprising: applying to fibrous material 4 a crosslinking composition comprising a photocatalyst and an active agent capable of crosslinking fibrous material 4; and then shaping the fibrous material 4 with the appliance 1 according to the first aspect. The crosslinking composition comprises a photocatalyst and an active agent capable of crosslinking fibrous material. In at least one embodiment, the active agent has at least two functional groups selected from the group consisting of: —NH$_2$, —NH—, —SH, —OH, —C(=O)H, —C=O, and COOH, and wherein the active agent has a molecular weight of 500 g/mol or less. In at least one embodiment, the active agent is a sugar. In at least one embodiment, the active agent is a reducing sugar. In at least one embodiment, the crosslinking composition comprises from about 0.1% to about 20.0%, or from about 2% to about 15%, or from about 5% to about 12% reducing sugar. In at least one embodiment, the active agent is selected from the group consisting of: arabinose, citric acid and ethylene carbonate, and mixtures thereof. In at least one embodiment, the photocatalyst is a hydroxy-substituted aromatic compound. In at least one embodiment, the crosslinking composition comprises a cosmetically acceptable carrier. In at least one embodiment, the cosmetically acceptable carrier is selected from either an aqueous medium or an aqueous-alcoholic medium. In at least one embodiment, when the carrier is an aqueous-alcoholic carrier, this carrier comprises water and an alcohol. In at least one embodiment, the alcohol is selected from the group consisting of: ethanol, isopropanol, propanol, and mixtures thereof. In at least one embodiment, the hydroxy-substituted aromatic compound is a quinoline compound or a naphthol compound. In at least one embodiment, the hydroxy-substituted aromatic compound is a fluorescein or a derivative thereof. In at least one embodiment, the hydroxy-substituted aromatic compound is a halogen-substituted fluorescein. In at least one embodiment, the hydroxy-substituted aromatic compound is bromo- or iodo-substituted fluorescein. In at least one embodiment, the hydroxy-substituted aromatic compound is selected from the group consisting of: diiodofluorescein, 4,5,6,7-tetrachloro-2',4',5',7'-tetraiodofluorescein (rose Bengal), a salt of 2,4,5,7-tetraiodofluorescein (erythrosine), Eosin Y, Eosin B, and mixtures thereof. In at least one embodiment, the hydroxy-substituted aromatic compound is a hydroxyflavone or a derivatives thereof. In at least one embodiment, the hydroxy-substituted aromatic compound is a dihydroxyflavone or a trihydroxyflavone or a tetrahydroxyflavone or a mixture thereof. In at least one embodiment, the hydroxy-substituted aromatic compound is selected from the group consisting of: 3-hydroxy flavones, 7-hydroxy flavones, 5,7-hydroxy flavones, 4',5,7-trihydroxyflavone, 2-(3,4-dihydroxyphenyl)-3,5,7-trihydroxy-4H-chromen-4-one (quercitin), and mixtures thereof. In at least one embodiment, the hydroxy-substituted aromatic compound is a hydroxyltriarylmethane, for example FD&C Green 3. In at least one embodiment, the hydroxy-substituted aromatic compound is an anthocyanidins or an anthocyanin. In at least one embodiment, the hydroxy-substituted aromatic compound is cyanidin (2-(3,4-dihydroxyphenyl) chromenylium-3,5,7-triol), malvidin, palargonidin or extracts containing anthocyanins such as elderberry, blueberry, cranberry, bilberry, red cabbage, sorghums, blackberry, black current, cherry red and black raspberry, and mixtures thereof.

In at least one embodiment, the hydroxy-substituted aromatic compound is selected from the group consisting of: 8-hydroxyquinoline, 8-hydroxyquinoline sulfate, 8-quinolinol-1-oxide, 5-hydroxyquinoline, 6-hydroxyquinoline, 7-hydroxyquinoline, 5-iodo-7-sulfo-8-hydroxyquinoline, 5-fluoro-8-hydroxyquinoline, 5-fluoro-7-chloro-8-hydroxyquinoline, 5-fluoro-7-bromo-8-hydroxyquinoline, 5-fluoro-7-iodo-8-hydroxyquinoline, 7-fluoro-8-hydroxyquinoline, 5-chloro-8-hydroxyquinoline, 5,7-dichloro-8-hydroxyquinoline, 5-chloro-7-brono-8-hydroxyquinoline, 5-chloro-7-iodo-8-hydroxyquinoline, 7-chloro-8-hydroxyquinoline, 5-bromo-8-hydroxyquinoline, 5-bromo-7-chloro-8-hydroxy quinoline, 5,7-dibromo-8-hydroxyquinoline, 5-bromo-7-iodo-8-hydroxyquinoline, 7-bromo-8-hydroxyquinoline, 5-iodo-8-hydroxyquinoline, 5-iodo-7-chloro-8-hydroxyquinoline, 5,7-diiodo-8-hydroxyquinoline, 7-iodo-8-hydroxyquinoline, 5-sulfonic acid-8-hydroxyquinoline, 7-sulfonic acid-8-hydroxyquinoline, 5-sulfonic acid-7-iodo-8-hydroxyquinoline, 5-thiocyano-8-hydroxyquinoline, 5-chloro-8-hydroxyquinoline, 5-bromo-8-hydroxyquinoline, 5,7-dibromo-8-hydroxyquinoline, 5-iodo-8-hydroxyquinoline, 5,7-diiodo-8-hydroxyquinoline, 7-azaindole, 7-cyano-2-naphthol, 8-cyano-2-naphthol, 5-cyano-2-naphthol, 1-hydroxy-3,6,8-pyrenetrisulfonic acid, Trans-3-hydroxystilbene, 2-hydroxymethylphenol, Pelargonidin, and mixtures thereof. In at least one embodiment, the hydroxy-substituted aromatic compound is selected from the group consisting of: 8-quinolinol-1-oxide, 8-hydroxyquinoline, 7-cyano-2-naphthol, 8-cyano-2-naphthol, 5-cyano-2-naphthol, and mixtures thereof. In at least one embodiment, the hydroxy-substituted aromatic compound is selected from the group consisting of: 8-quinolinol-1-oxide, 8-hydroxyquinoline, and mixtures thereof. In at least one embodiment, the hydroxy-substituted aromatic compound is 8-hydroxyquinoline. 8-hydroxyquinoline may act as a photoacid catalyst in lower pH solutions or as a photobase catalyst in higher pH solutions. 8-hydroxyquinoline has the CAS Number 148-24-3 and is available from Sigma-Aldrich.

$3^{rd}$ Aspect—Use

The third aspect relates to the use of the appliance according to the first aspect for shaping fibrous material 4, preferably straightening hair. In at least one embodiment, the use is for smoothing hair. In at least one embodiment, the use is for repairing hair.

4th Aspect—Kit

The fourth aspect relates to a kit. The kit comprises: the appliance 1 according to the first aspect; and a crosslinking composition comprising a photocatalyst and an active agent capable of crosslinking fibrous material 4. Features of the crosslinking composition are described in the second aspect and said description and features are compatible and combinable with the 4th aspect.

Methodology/Experimental

Figure 11:
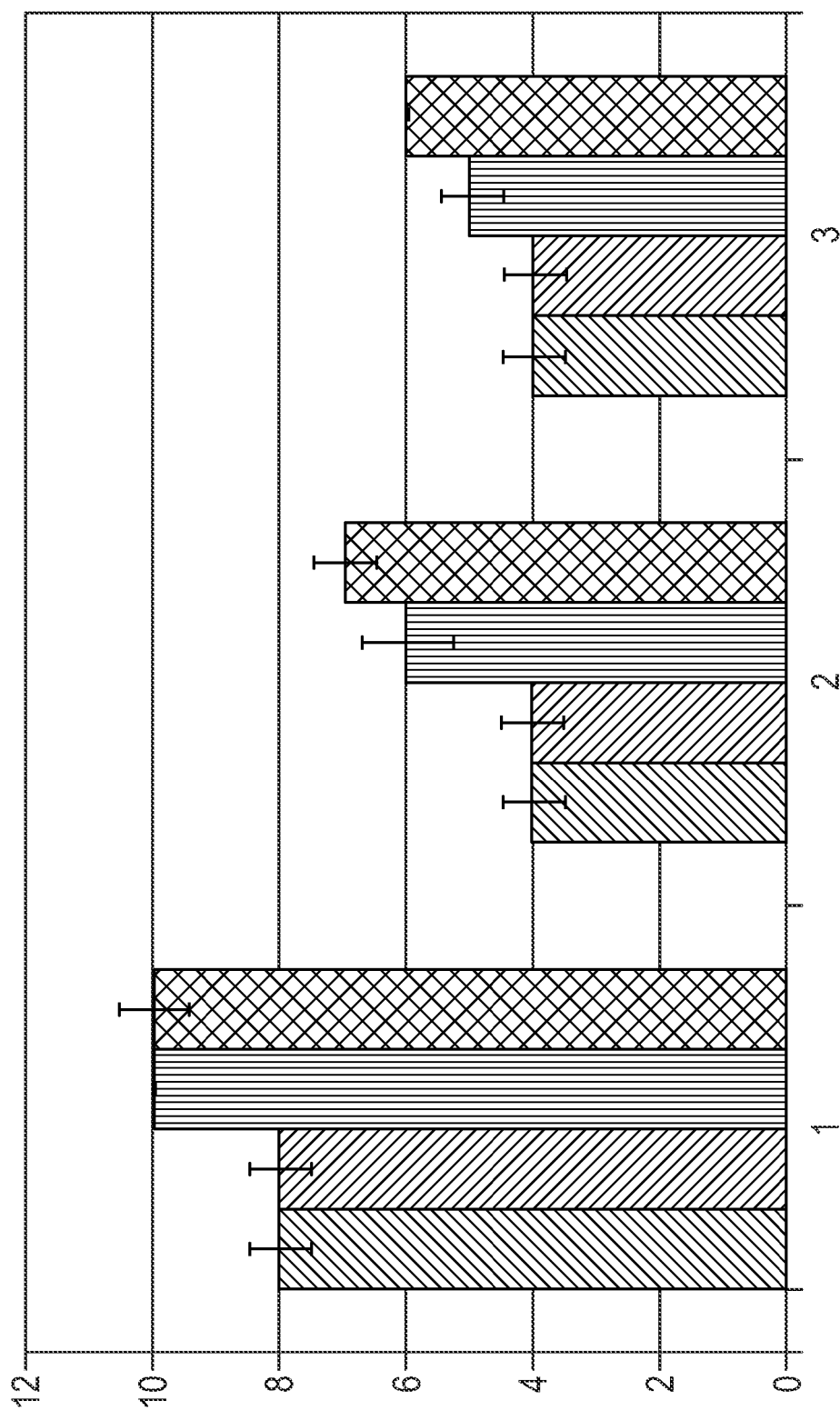
FIG. 11: Shows human scalp hair straightness analysis. Arabinose as active agent in the crosslinking composition is tested. The y axis is the straightness score. The effect of different treatment conditions is compared as is the durability of these treatments to hair washing. Numbering along the x axis: 1=immediately after the flat iron treatment; 2=after the 1$^{st}$ wash-and-dry cycle; 3=after the 5$^{th}$ (i.e. 4 further) wash-and-dry cycles. Upward-striped bars (far left)=no crosslinking composition is used and hair switches are treated with hair straightening irons at 250° F. (121° C.). Downward-striped bars=no crosslinking composition is used and hair switches treated with an appliance according to the present invention at 250° F. (121° C.). Vertical-striped bars=switches are treated with a crosslinking composition comprising 5% arabinose, 200 ppm photocatalyst and water (buffered to pH10) and the switches are then treated with heated hair straightening irons at 250° F. (121° C.). Crosshatched bars=switches are treated with a crosslinking composition comprising 5% arabinose, 200 ppm photocatalyst and water (buffered to pH 10) and the switches are then treated with an appliance according to the present invention at 250° F. (121° C.).

The hair straightening efficacy is tested for the appliance of the present invention. Switches of low lift naturally curly hair are employed. These are shampooed with a Pantene clarifying shampoo to ensure the hair is in a clean state with no residues that could affect the end result. The switches are then rinsed. Excess water is removed from the hair by wringing out the switches. The switches are treated with a crosslinking composition which is pre-prepared in a dark room. The crosslinking composition comprises: 5% arabinose; 100 ppm 8-hydroxyquinoline; 100 ppm 8-quinolinol-1-oxide; QSP water buffered to pH 10. These ingredients are mixed on a spinner plate for 30 mins. The crosslinking composition is stored in an amber bottle or a bottle covered in electrical tape to ensure no light access to the crosslinking composition. 0.25 g of crosslinking composition per 1 g hair is employed. The crosslinking composition is left on the hair for 30 minutes. As a control experiment, hair switches are treated exactly the same but no crosslinking composition is applied to the switch—the control switches are allowed to rest damp for 30 minutes. After this time, the hair is blow dried and brushed. The switches are then mechanically straightened with an appliance according to the present invention with 8 passes or with conventional heated hair straightening irons. The appliance used comprises a heating element 9 is provided in both the first arm 2 and the second arm 3; and a light source 10 is provided in both the first arm 2 and the second arm 3. The switches are then imaged. To simulate durability, the switches are then given one wash-and-dry cycle. One wash-and-dry cycle involves shampooing with a Hairtrition shampoo (Hairtrition Color Protect sulfate-free shampoo from Zotos), rinsing and then drying in a hot box. Once dry the switches are imaged again. The switches are then given 4 further wash-and-dry cycles. Once dry the switches are imaged again. An expert grader gives the images of the switches a score on a 0-10 scale. The scale is a standard scale set as curly hair having 4-5 nodes of curls is a score of 0 and very straight hair is a 10. Thus, the switches are compared to a normal state of hair. Using an expert grader is reliable because the grader is trained on measuring/scaling the configuration of the hair from straight to curly in a consistent way. The results are shown in FIG. 11. Referring to this FIG., the numbering along the x axis: 1=immediately after the flat iron treatment; 2=after the 1st wash-and-dry cycle; 3=after the 5th (i.e. 4 further) wash-and-dry cycles. Upward-striped bars (far-left)=no crosslinking composition is used and hair switches are treated with conventional heated hair straightening irons at 250° F. (121° C.). Downward-striped bars=no crosslinking composition is used and hair switches treated with an appliance according to the present invention at 250° F. (121° C.) and emitting UV light at 380 nm and a radiant power of 30 mW. Vertical-striped bars=switches are treated with a crosslinking composition comprising 5% arabinose, 200 ppm photocatalyst and water (buffered to pH10) and the switches are then treated with conventional heated hair straightening irons at 250° F. (121° C.). Cross-hatched bars=switches are treated with a crosslinking composition comprising 5% arabinose, 200 ppm photocatalyst and water (buffered to pH 10) and the switches are then treated with an appliance according to the present invention at 250° F. (121° C.) and emitting UV light at 380 nm and a radiant power of 30 mW.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or patent publication, is hereby incorporated herein by reference in its entirety unless expressly excluded or otherwise limited. The citation of any document is not an admission that it is prior art with respect to any document disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An appliance (1) for shaping fibrous material (4) comprising:
   a first arm (2) pivotable with respect to a second arm (3), the first arm (2) and the second arm (3) thereby configured to form a clamp for receiving fibrous material (4) positioned between the first and second arms (2, 3) when the appliance is in a closed position;
   wherein the first arm (2) comprises a first inner face (5) which faces the second arm (3);
   and wherein the second arm (3) comprises a second inner face (6) which faces the first inner face (5) on the first arm (2);
   and wherein a first plate (7) extends upon a portion of the first inner face (5);
   and wherein a second plate (8) extends upon a portion of the second inner face (6);
   wherein both the first plate (7) and the second plate (8) are substantially flat;
   wherein a heating element (9) is provided in at least one of the first arm (2) and/or the second arm (3);
   wherein at least one light source (10) is provided in at least one of the first arm (2) and/or the second arm (3);
   and wherein the first inner face (5) and/or the second inner face (6) respectively comprise a heat-transmitting area (11) and/or a light-transmitting area (12);
   and wherein the heating element (9) is located proximal to the heat-transmitting area (11) and wherein the light source (10) is located proximal to the light-transmitting area (12);

and wherein when the appliance (1) is in the closed position, the portion of the fibrous material (4) received between the first inner face (5) and the second inner face (6) can receive light energy from the light source (10) and heat energy from the heating element (9);

wherein the light energy comprises ultraviolet light;

wherein the light source is surrounded by a light protector to protect the user from said ultraviolet light when the appliance is in operation; and wherein the appliance further comprises a magnetic switch disposed in the arms of the appliance whereby the light source receives power only when said arms are in a closed position.

2. The appliance (1) of claim 1, wherein the light source (10) is capable of emitting light having a wavelength of from about 315 nm to about 450 nm.

3. The appliance (1) of claim 1, wherein the light source (10) is capable of emitting light having a wavelength of from about 350 nm to about 440 nm.

4. The appliance (1) of claim 1, wherein the light source (10) is at least one light-emitting diode.

5. The appliance (1) of claim 1, wherein the light source (10) is a plurality of light-emitting diodes disposed along at least a portion of the length of the first and/or second arm (2, 3).

6. The appliance (1) of claim 5, wherein the light source (10) comprises at least two arrays of light-emitting diodes, wherein each array is a plurality of light-emitting diodes disposed along at least a portion of the length of the first and/or second arm (2, 3).

7. The appliance (1) of claim 1, wherein the light source (10) has an illuminance of at least about 7000 lx.

8. The appliance (1) of claim 1, wherein the light-transmitting area (12) is not in a plane with the heat-transmitting area (11).

9. The appliance (1) of claim 1, wherein the heat-transmitting area (11) or the fibrous material (4) can be heated to a temperature of from about 50° C. to about 180° C.

10. The appliance (1) of claim 1, wherein the the first arm (2) and the second arm (3) each comprise a handle portion (20, 20') being distal from the heat-transmitting area (11).

11. The appliance (1) of claim 1, wherein when the appliance (1) is in the closed position, the portion of the fibrous material (4) received between the first inner face (5) and the second inner face (6) can simultaneously receive light energy from the light source (10) and heat energy from the heating element (9).

12. The appliance (1) of claim 1, wherein the first arm and the second arm are connected by a hinge (17), and wherein the handle portion of each arm (2, 3) is proximal to the hinge (17).

13. The appliance (1) of claim 1, wherein the light source (10) is insulated from the heating element (9), or wherein the light source (10) is cooled.

14. The appliance (1) of claim 1, wherein the first and/or second plate (7, 8) are composed of ceramic and the ceramic is transparent to infrared light and wherein the heating element (9) is an infrared heater.

15. The appliance (1) of claim 14, wherein the light source (10) is isolated from the heating element (9) and heat-transmitting area (11) via an insulating means (15); wherein the insulating means (15) is an area of air and/or insulating material.

16. The appliance (1) of claim 1, wherein the appliance (1) has a sensor that measures data from which a parameter based on the condition of the fibrous material (4) can be generated, and wherein the parameter influences the temperature of the heating element (9).

17. A method for shaping fibrous material (4) comprising:
applying to fibrous material (4) a crosslinking composition comprising a photocatalyst and an active agent capable of crosslinking fibrous material (4); and then
shaping the fibrous material with the appliance (1) according to claim 1.

18. A kit comprising:
the appliance (1) according to claim 1;
a crosslinking composition comprising a photocatalyst and an active agent capable of crosslinking fibrous material (4).

* * * * *